(12) United States Patent
Craig

(10) Patent No.: US 6,381,967 B1
(45) Date of Patent: May 7, 2002

(54) CRYOGENIC FREEZING OF LIQUIDS

(76) Inventor: Randall H Craig, 3200 N. Dobson Rd., #F7, Chandler, AZ (US) 85224

( * ) Notice: Subject to any disclaimer, the term of this patent is extended or adjusted under 35 U.S.C. 154(b) by 0 days.

(21) Appl. No.: 09/486,447

(22) PCT Filed: Nov. 24, 1998

(86) PCT No.: PCT/US98/25365
§ 371 Date: Feb. 24, 2000
§ 102(e) Date: Feb. 24, 2000

(87) PCT Pub. No.: WO99/66271
PCT Pub. Date: Dec. 23, 1999

Related U.S. Application Data

(60) Provisional application No. 60/089,683, filed on Jun. 17, 1998.

(51) Int. Cl.[7] .............................................. F25D 17/02
(52) U.S. Cl. ............................. 62/64; 34/284; 62/54.1; 62/78; 62/346; 435/307.1
(58) Field of Search .............................. 62/78, 64, 54.1, 62/346; 435/307.1; 34/284

(56) References Cited

U.S. PATENT DOCUMENTS

| | | | |
|---|---|---|---|
| 4,704,873 A | * 11/1987 | Imaike et al. ................... | 62/78 |
| 4,799,361 A | 1/1989 | Linner | |
| 5,275,016 A | 1/1994 | Chatterrjee et al. | |
| 5,279,609 A | 1/1994 | Meckler | |
| 5,644,922 A | 7/1997 | Linden et al. | |
| 5,664,422 A | 9/1997 | Jones | |
| 5,715,686 A | * 2/1998 | Arav ............................... | 62/78 |
| 5,780,295 A | * 7/1998 | Livesay et al. .......... | 435/307.1 |

* cited by examiner

*Primary Examiner*—Ronald Capossela
(74) *Attorney, Agent, or Firm*—Oppedahl & Larson LLP

(57) ABSTRACT

The invention relates to method and apparatus for the hyper-rapid freezing of liquid samples. The samples are converted into droplets or vapor and rapidly driven directly onto the surface of a solid or slushed refrigerant.

64 Claims, 8 Drawing Sheets

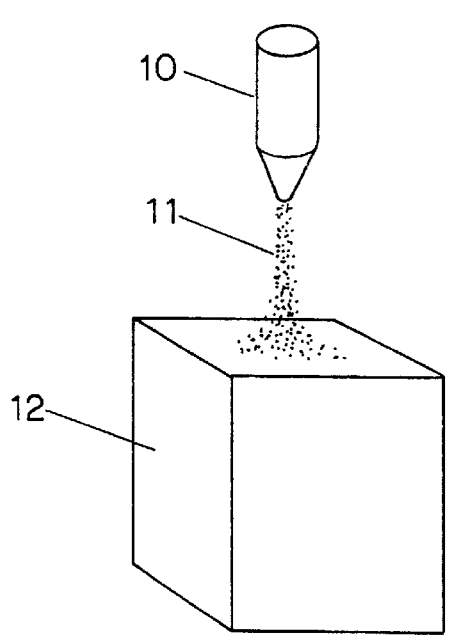
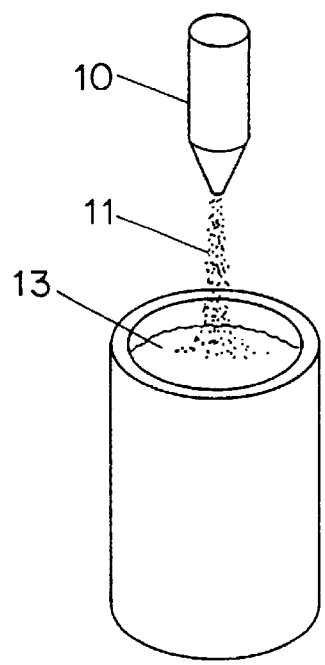
FIG. 1A          FIG. 1B
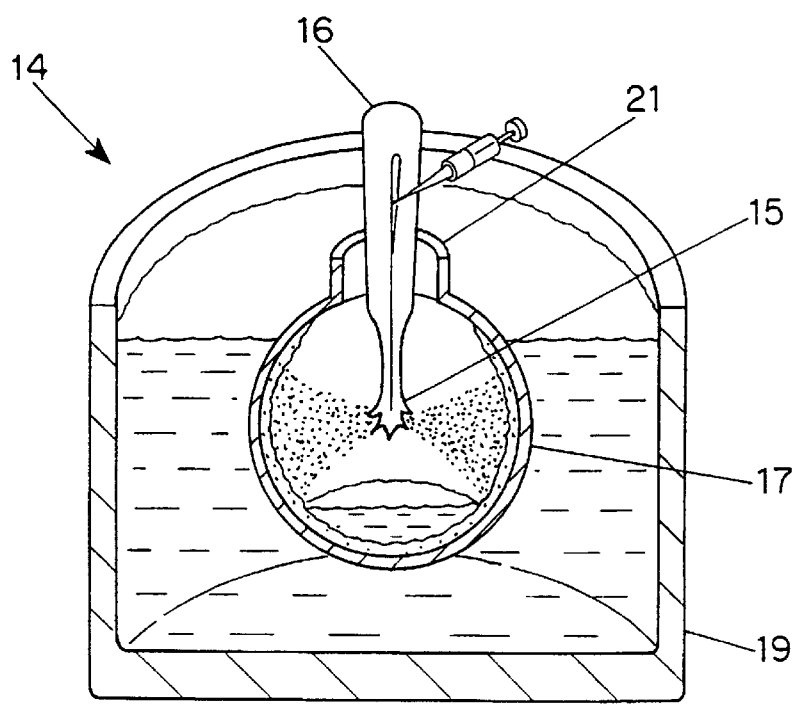
FIG. 2

CRYOGENIC FREEZING OF LIQUIDS

This application claims priority from U.S. Provisional Application Ser. No. 60/089,683, filed Jun. 17, 1998, which is hereby incorporated herein by reference.

BACKGROUND OF THE INVENTION

1. Field of the Invention

This invention relates to methods and apparatus for preservation of specimens by hyper-rapid freezing. More particularly, the present invention relates to methods for hyper-rapid freezing of liquid biological specimens utilizing solid or slushed refrigerants.

2. Description of the Related Art

Freezing has been defined as the solidification of a liquid and may be divided into two kinds: crystallization and vitrification. Crystallization involves an orderly arrangement of molecules, while vitrification is the glass-like solidification of solutions at low temperature without ice crystal formation. Vitrification can be achieved by increasing the viscosity of the solution and by high speeds of cooling and warming. Within certain limits, the higher the speed of the temperature change, the lower the viscosity required to vitrify.

Dubochet, et al. (J. Microscopy, vol. 124, pt. 3, pp. RP3-RP4, 1981) describes novel methods and apparatus for ultra-rapid vitrification of water. Successful vitrification of pure water was achieved by spraying water onto a wire screen and dropping the screen into liquid nitrogen. Microscopic examination of sections of the frozen film of water revealed that the regions near the surface had been vitrified into a noncrystalline glass, although regions where the water film was thicker had frozen into small crystals. Apparently, heat from the water film could be transferred rapidly enough into liquid nitrogen to freeze water into a glass structure before ice crystals had a chance to form. The key to success of the experiment was the high surface to volume ratio (film) of the water, and the rapid decrease in temperature provided by the plunge into liquid nitrogen.

Rapid water vitrification requires extremely rapid freezing rates. Ice crystal size depends primarily on how rapidly heat is removed from the freezing sample. Faster freezing rates lead to smaller ice crystals. If heat energy can be removed quickly enough, then ice crystals will become vanishingly small, and, at fast enough freezing rates, ice crystals will not form at all. Instead, the water molecules slow their movement so quickly they do not have time to form a crystal lattice, and will solidify into a disorganized glass-like structure, i.e. vitrify.

Water molecules are very polarized, and therefore easily form crystal lattices when frozen. Compared to other compounds, the rate of freezing pure water into a vitreous state is extraordinarily rapid on the order of $-1,000,000°$ F./sec. This freezing rate is so high that in the past, vitrification of pure water was thought to be virtually impossible, and currently only a few technological methods exist that are capable of vitrifying very small quantities of water.

Preservation of biological specimens for future use has long been a goal of the scientific community. Successful methods such as freezing and freeze drying have been achieved for simple biological specimens. Many complex macromolecules and whole cells show reduced activity or viability following freezing or freeze drying by conventional methods.

In general, cell injury or cell death from freezing occurs from one (or both) of two mechanisms. The first mechanism is growing ice crystals, which injure cell membranes and organelles due to their sharp edges. Usually, the ice crystals form and grow primarily in the extracellular space and encroach upon the cell from outside. As freezing progresses, the (relatively) large ice crystals damage or puncture the cell membrane and distort the shape and overall structure of the entire cell. As the freezing process nears completion, intracellular ice formation may also form, with internal ice crystals causing physical damage to organelles and other cellular structures.

The second mechanism is internal cell "poisoning" which results from very high concentrations of intracellular solutes, created by osmotic dehydration. As freezing progresses, extracellular ice crystals form and grow larger. The ice is relatively pure water, and ice crystal growth consumes extracellular liquid water which then increases the extracellular solute concentrations. An osmotic force is created between the intracellular and extracellular spaces which drives water across the cell membrane out of the cell. As extracellular water is consumed by ice growth, it is replaced by intracellular water and the cell becomes osmotically dehydrated. Increasing concentrations of various solutes inside the cell eventually reach toxic levels, damaging or killing the cell.

Both mechanisms operate simultaneously during cell or tissue freezing processes using most current technologies. Balancing the influence of each mechanism to minimize cell damage during freezing and thawing is the goal of any cryopreservation process.

High cooling rates are necessary to freeze biological specimens while avoiding ice crystal formation and maintaining in situ diffusible chemical components. The conventional method is plunging cryoprotected biological specimens into a cooling liquid such as liquid nitrogen. This method may be used in the absence of cryoprotectants if the specimens are thin and mounted on low-mass sample holders and the coolant around the sample is renewed fast enough to prevent the formation of a gaseous layer which would limit heat transfer (Escaig, J. Microscopy, vol. 126, pt 3, pp. 221–229, 1982). Another method in which cryoprotectants are not required is contacting the specimen with a metal block cooled to the temperature of liquid nitrogen or helium (Escaig 1982; Sitte, et al., J. Microscopy, vol. 111, pt 1, pp 35–38, 1977). Problems associated with these methods include the difficulty of making suitable specimen holders and the lack of reproducibility of freezing.

Another approach to preserving biological specimens is freezing under high pressure. Conaway (U.S. Pat. No. 4,688,387) teaches placing the biological specimen into a pressure vessel, applying high pressure to the specimen, and then placing the pressure vessel into liquid nitrogen to achieve cooling. A disadvantage of this method is that long term storage at high pressure and low temperature is not convenient. Therefore, once the specimen is frozen, the pressure is released and the specimen is stored at low temperature. However, the specimen must be placed under high pressure again prior to thawing.

Most protein and peptide specimens exhibit poor survival during the conventional freeze-thaw or freeze-dry processes, with low recoveries of 40% to 90% of the original specimen. This is attributed to physical injury and loss of structural integrity of the protein molecule, presumably from water crystal or osmotic damage during the freezing process.

Cryopreservation agents may be added or controlled freezing rates used in order to maximize cell survival. Cryopreservation agents, such as DMSO or propylene glycol, reduce the freezing temperature point and ice crystal size, and at optimal concentrations the cryopreservation agents will significantly increase cellular freeze-thaw survival. However, excessive concentrations of cryopreservatives are toxic to cells and tissue, limiting their usefulness. Controlled freezing rates allow better optimization of the two cell damage mechanisms at different times during the freezing process, and use of plateau and stopping points to permit ice crystal seeding further enhances cell survival for some processes. Optimal freeze-thaw survival for some current applications requires a complex process of cell preparation, changing concentrations of cryopreservation agents, multi-step freezing rates, multiple ice crystal seedings, and finally a rapid plunge into liquid nitrogen or other cryogenic liquefied gas to vitrify the remaining liquid that had not already frozen into ice crystals. Complex thawing protocols may also be required to minimize ice crystal or hyper-concentrated solutes from further damaging the cells.

Several types of biological specimens have been successfully frozen and thawed using cryopreservatives and various freezing rates. Examples include plant material, tissue culture cells, sperm and embryos. Oocytes, however, are particularly difficult to cryopreserve for the following reasons:

1) High volume-to-surface ratio. Oocytes are the largest cells of the mammalian body. During equilibration, high concentration gradients of cryoprotectants may arise resulting in toxic damage in one part of the cell and insufficient protection in the other part of the cell. Osmotic effects are also increased and during equilibration and dilution oocytes may suffer extreme changes of shape resulting in possible damages of membranes and cytoskeleton.

2) Chilling injury. In bovine oocytes, low temperature sensitivity is attributed to two different factors. Besides damage of the numerous lipid droplets, the meiotic spindle of the metaphase II oocytes suffers serious injury when cooled to 4 or even 25° C. Unlike the lipid alteration, damage to the spindle after short-time low-temperature exposure is reversible, but may even so disturb the subsequent fertilization process.

3) Alteration of the zona pellucida. Cooling may result in decreased fertilization rates caused by premature cortical granule exocytosis and zona hardening.

4) Cumulus cell removal. Both immature and mature oocytes form a functional unit with the attached cumulus cell layers. Unlike the in vivo process, the cumulus investment is beneficial for in vitro fertilization either by promoting sperm capacitation or preventing polyspermy. However, these layers and the accumulated glycoproteins reduce the speed of cryoprotectant penetration either at equilibration or at dilution. In a group of oocytes, partial removal of cumulus cells is very difficult to perform uniformly, and the differences may result in uneven cryoprotectant penetration (Vajta, IETS Newsletter, June 1997, http://www.iets.uiuc.edu/news/iets697.html#featured). The damage sustained is often enough to kill the cell or prevent if from successfully fertilizing.

Martino, et al (Biology of Reproduction, vol. 54, pp 1059–1069, 1996) discloses a method for cryopreserving bovine oocytes in which oocytes were placed in a cryopreservative medium, and placed either in straws or on electron microscope grids. The straws were plunged into liquid nitrogen and the grids were either plunged into liquid nitrogen or nitrogen slush. Martino, et al. report that cooling rates achieved with grids were much higher than with straws. To test whether the use of even faster cooling rates would improve survival, nitrogen slush was compared to liquid nitrogen for freezing oocytes on grids. Survival rates based on morphology, cleavage and blastocyst formation were higher for oocytes frozen in liquid nitrogen compared to those frozen in nitrogen slush.

Successful cryopreservation of biological specimens without the risk of cryoprotectant toxicity and loss of viability common with current methods would have significant clinical and scientific applications. Successful cryopreservation of human oocytes would have significant clinical applications, including frozen quarantine of donor eggs to prevent HIV or hepatitis transmission to the recipient, long-term storage of oocytes for chemotherapy patients who wanted to later attempt pregnancy, or for women undergoing oophorectomy for benign disease, or for short-term storage for women with ovarian hyper-stimulation syndrome.

The practice of freezing and storing sperm and embryos has achieved a certain amount of success. Freezing and thawing unfertilized oocytes, however, has not generally been successful for reasons set forth above. The ability to freeze and store oocytes and sperm separately would avoid the legal complications regarding custody and maintenance of frozen embryos. The instant invention is particularly useful for freezing unfertilized oocytes.

SUMMARY OF THE INVENTION

An embodiment of the instant invention is a method of rapidly freezing and storing water or liquid samples without the use of cryoprotectants to minimize or eliminate damage from ice crystals or osmotic forces, allowing very high recovery rates upon thawing. The liquid sample is transformed into very small drops which are contacted directly with a refrigerant which is at least partially solidified. The refrigerant may be a solid undergoing a solid-to-liquid phase change, or a solid-to-gas phase change. This method is especially useful for substances that are susceptible to ice crystal or osmotic damage, such as proteins, peptides, and other macromolecules.

A further embodiment of the invention is a method of stopping a chemical or biological reaction by rapidly freezing the reaction mixture through direct contact with a refrigerant which is at least partially solidified. Molecular slowing occurs almost instantly, preserving the compounds in mid-reaction. The various molecular steps of the reaction are frozen in place, and can be analyzed by studying the vitrified sample.

A further embodiment of the invention is to provide a method for lyophilizing chemical and biological compounds or compositions while retaining structural integrity. Reconstitution of the substance will restore the original liquid sample with little or no damage. Specific applications of this type of lyophilization include freeze dried foodstuffs (coffee, milk, juices, etc.), medical supplies (vaccines, antibiotics, etc.) and laboratory processes (protein extractions, molecular biology samples, etc.).

An additional embodiment of the invention is a method for production of fine-grained or amorphous solids by direct deposition of a vapor substance onto a cryogenic gas which is at least partially solidified.

Another embodiment of the invention is an apparatus for rapid freezing a liquid sample. The apparatus comprises a means for driving the liquid sample directly onto a refrigerant which is at least partially solidified. Another embodiment of the apparatus is one which further comprises a means for transforming the liquid sample into very small drops prior to driving them onto the refrigerant.

A method was developed for rapidly freezing a sample in which primary and secondary refrigerants in thermal contact are used to achieve the state of at least partial solidification of the primary refrigerant. Another method for achieving a state of at least partial solidification of the primary refrigerant is evaporative cooling by placing the refrigerant in a vacuum chamber and subjecting it to low pressure.

Various additional features can be included in further embodiments of the invention. One such feature is an apparatus with multiple freezing chambers. Another feature is an apparatus with a continuously renewed solidified primary refrigerant surface. Additional features include apparatus for direct injection of sample onto solid or into partially solidified refrigerant.

An additional embodiment of the invention is a method for rapidly freezing non-liquid samples by contacting them directly with a refrigerant which is at least partially solidified.

BRIEF DESCRIPTION OF THE DRAWINGS

FIGS. 1A and 1B are illustrations of the basic method of this invention.

FIG. 2 is a cross-sectional view of an embodiment of the hyper-rapid freezing device involving primary and secondary refrigerants.

DETAILED DESCRIPTION OF THE INVENTION

Figure 3:
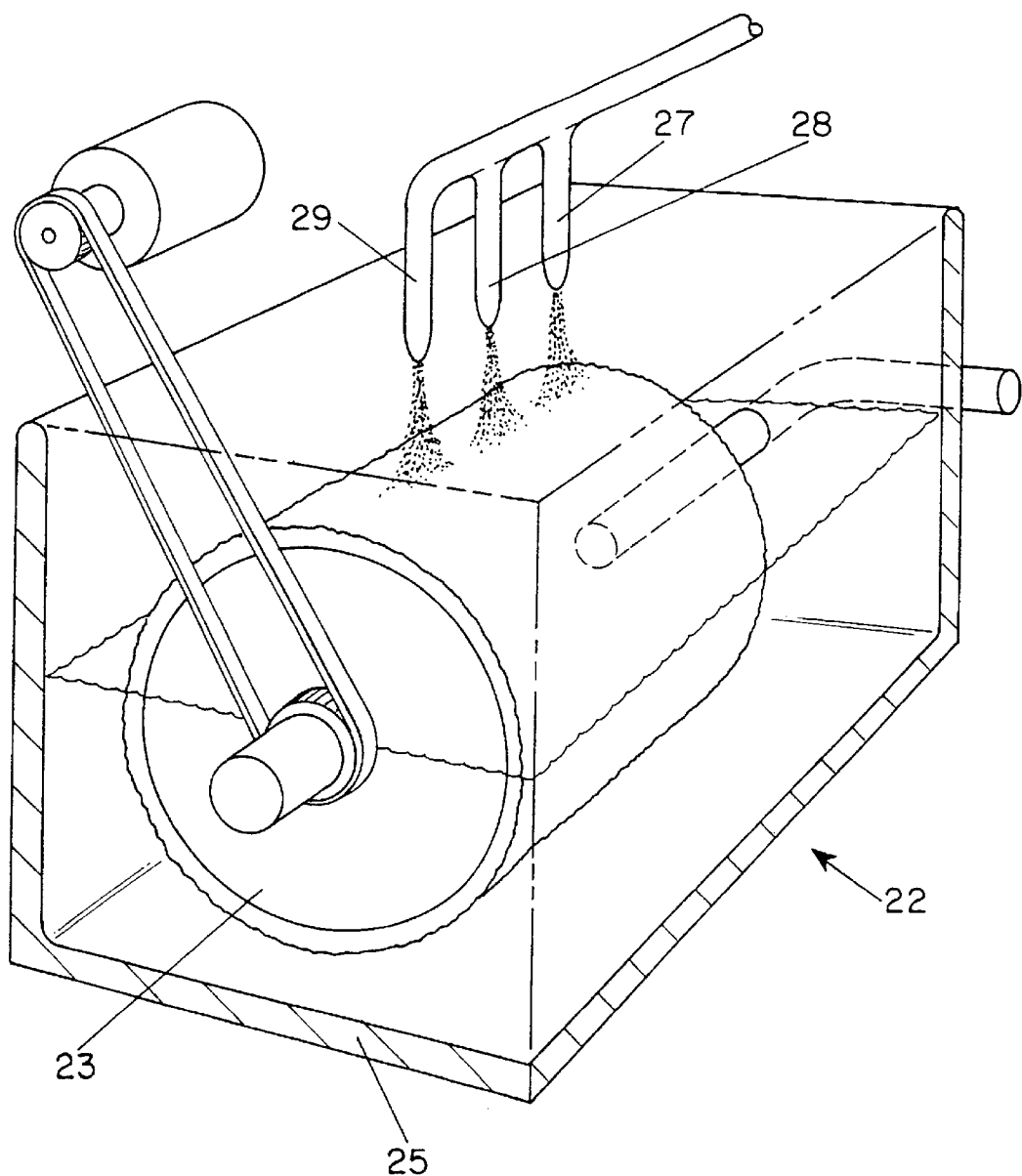
FIG. 3 is a perspective view of a device for hyper-rapid freezing with a continuously renewed solidified argon surface.
Figure 4:
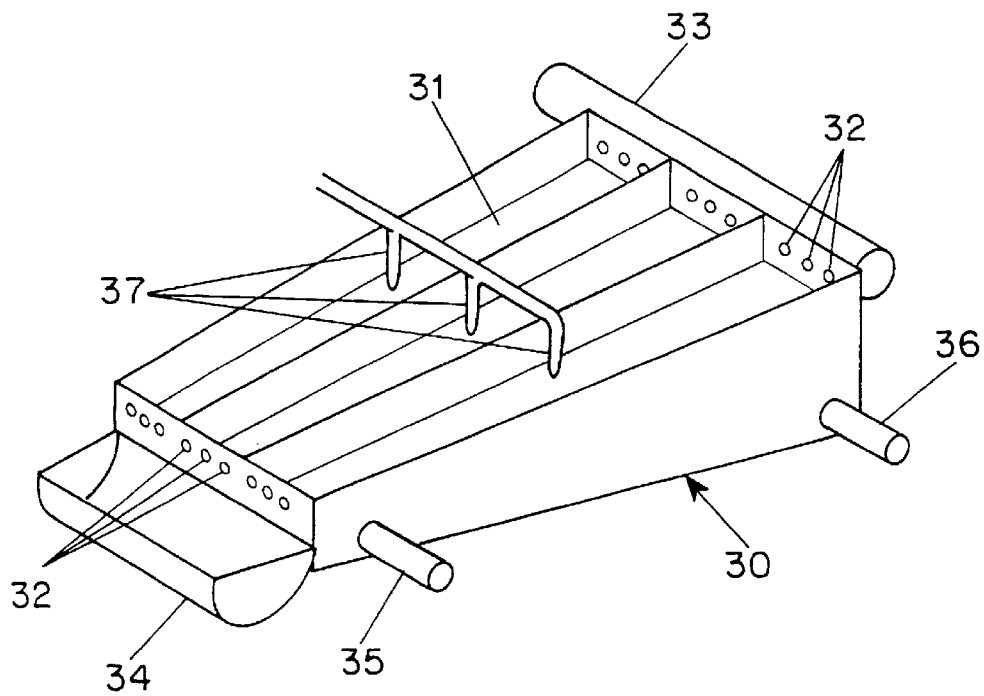
FIG. 4 is a perspective view of a device for continuous hyper-rapid freezing.
Figure 5:
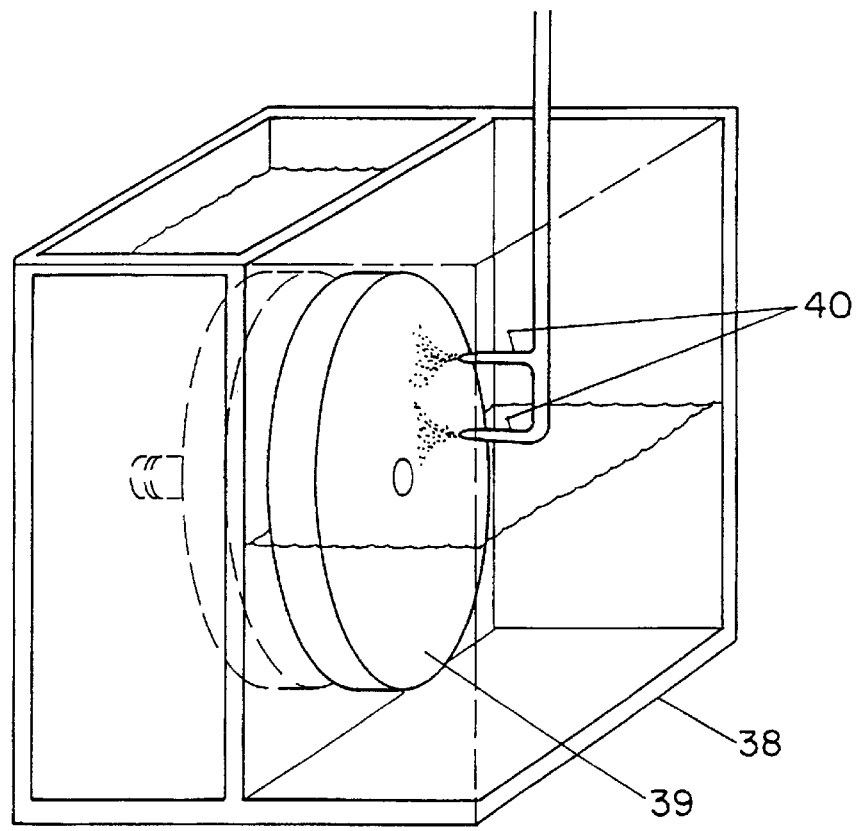
FIG. 5 is a perspective view of a device for hyper-rapid freezing with a continuously renewed solidified argon surface.
Figure 6:
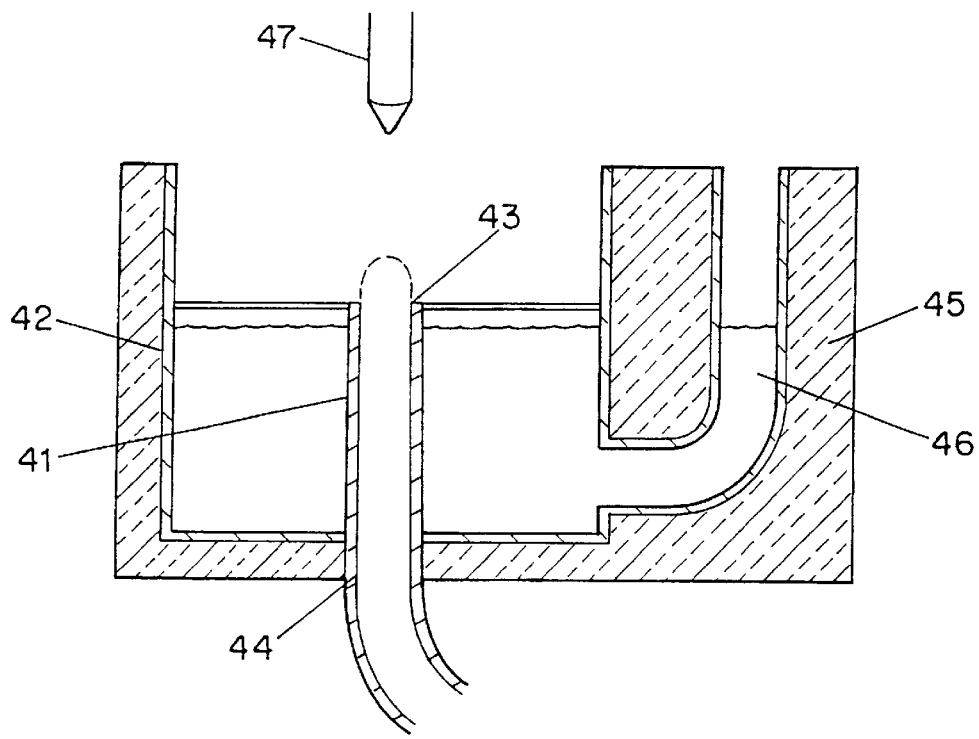
FIG. 6 is a cross-sectional view of a device for hyper-rapid freezing with a continuously renewed solidified argon surface.
Figure 7:
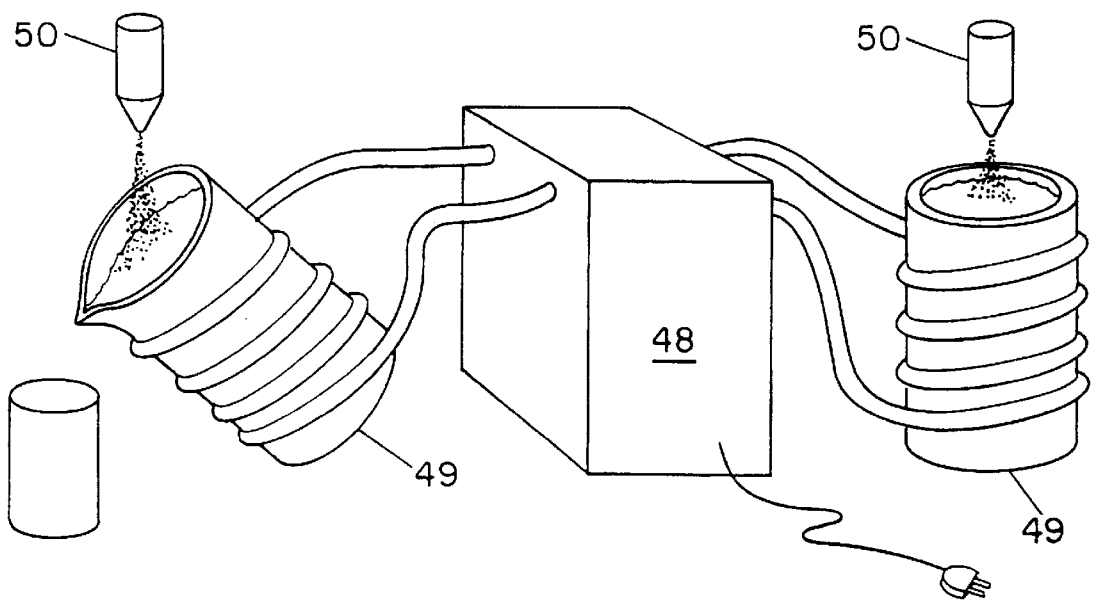
FIG. 7 is a perspective view of a device for hyper-rapid freezing utilizing mechanical refrigeration.
Figure 8:
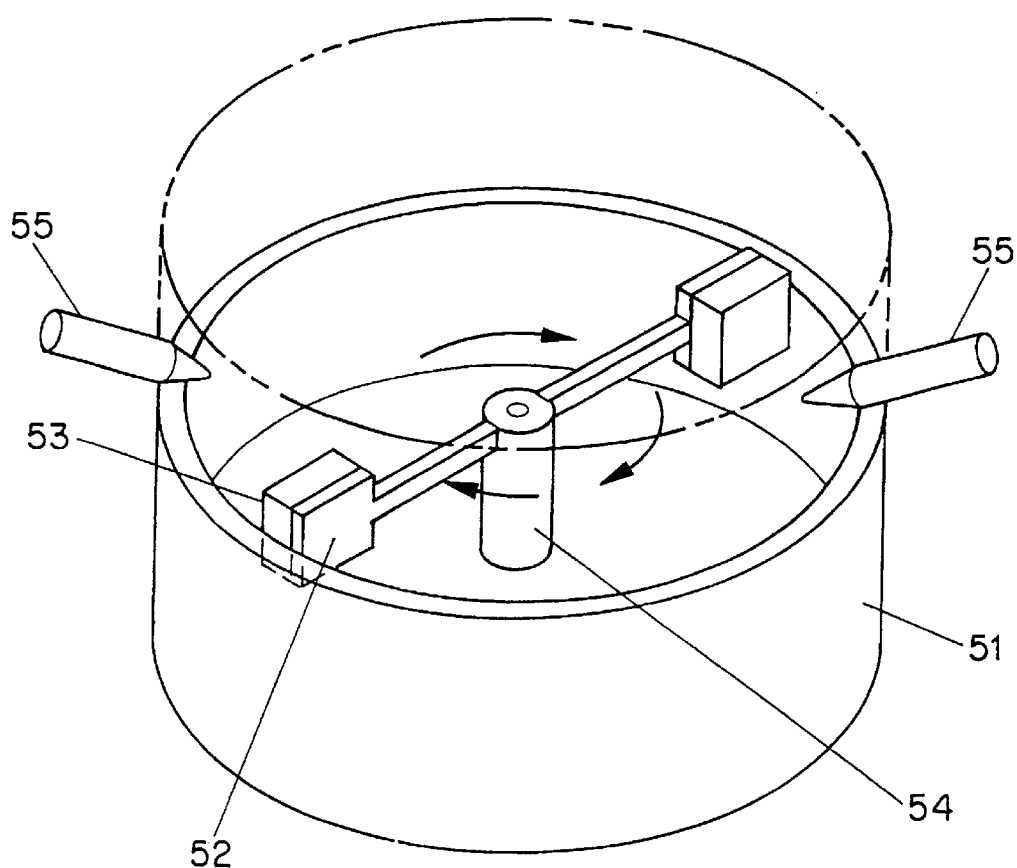
FIGS. 8, 9 and 10 are perspective views of devices for hyper-rapid freezing utilizing centrifugation.
Figure 9:
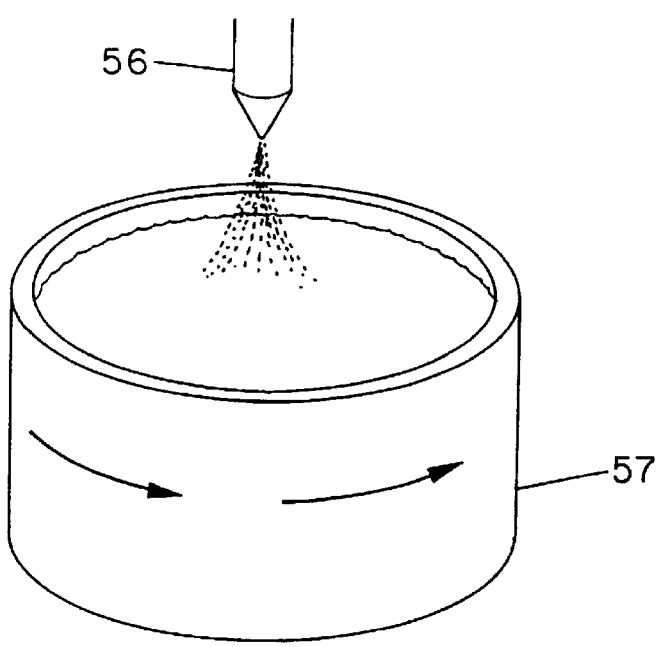
Figure 10:
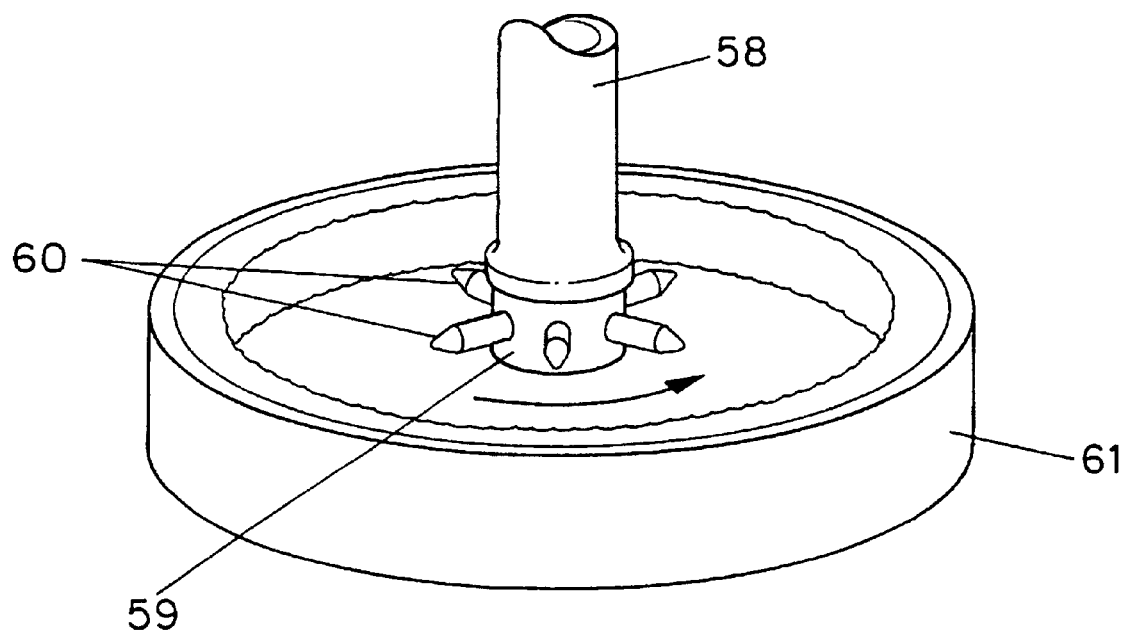
Figure 12:
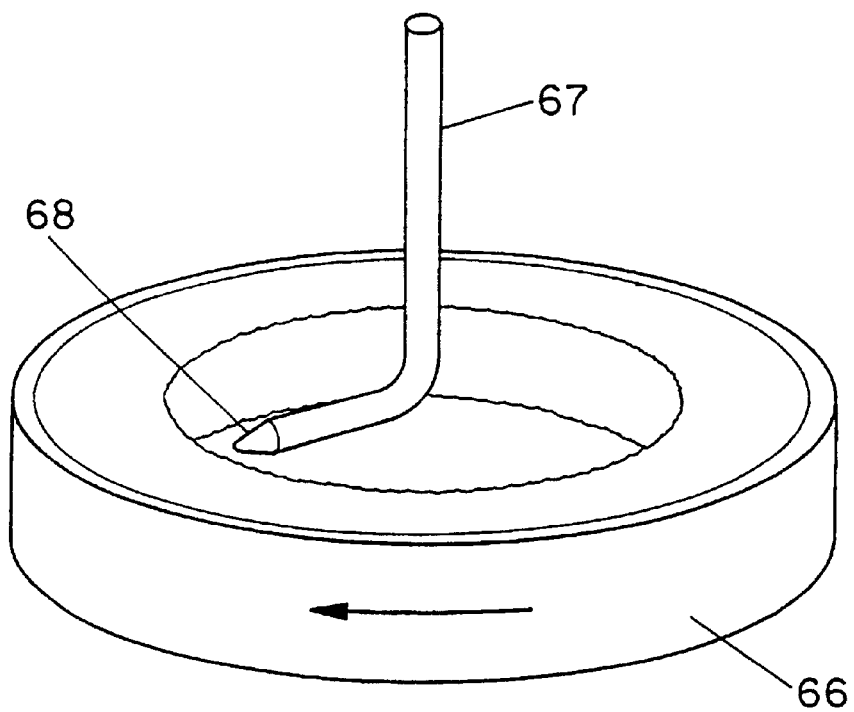
FIG. 12 is a perspective view of a device for hyper-rapid freezing utilizing direct injection of sample onto solid refrigerant.

The most basic element of this rapid freezing method is bringing small liquid drops or particles into direct contact with a refrigerant which is at least partially solidified, and collecting the frozen liquid. A variety of devices and processes can be used to implement this basic method. The simplest version of this embodiment is spraying a nebulized or atomized liquid directly onto the refrigerant's surface. This embodiment of the invention is illustrated in FIGS. 1A and 1B. A nebulizer 10 converts the sample into very small droplets 11 which contact solid 12 or slushed 13 primary refrigerant.

As used herein, the terms "collect" and "collecting" shall refer to the process of recovering the frozen material for transport. Thus, the term "collecting" will include creating the frozen material in a container suitable for transport and storage, such that the freezing and the collecting steps occur concurrently.

The phase change of the refrigerant from solid to at least partially solidified to liquid is a key element of this process. The phrase "at least partially solidified" is intended to encompass completely solid and slush phases. The term "slush" is intended to encompass liquid that has just begun to solidify through equal parts solid and liquid up to the point just before complete solidification. In a slush, the ratio of solid to liquid components is such that movement of particles of solid is controlled by the liquid component. The solid and liquid components of a slush may be the same element or compound or may be different elements or compounds. A slush includes stable mixtures of liquid and solid substantially at equilibrium. When the solid and liquid components are different elements or compounds, the elements or compounds must be compatible in terms of providing an environment suitable for freezing the sample.

A large number of substances can be employed as the refrigerant, depending on the temperature range desired and the composition of the liquid drops to be frozen. It should be understood that "refrigerant" includes substances with a temperature less than or equal to 0° C. When two or more refrigerants are used, the entire system has a temperature less than or equal to 0° C. Refrigerants can be selected from several basic types, including chemical elements and compounds, organic substances or mixtures of these items. Examples of elements include helium (under pressure), hydrogen, nitrogen, argon, neon, krypton, xenon, oxygen, mercury, gallium, and lead. An example of a compound is water and carbon dioxide (under pressure). Examples of organic substances include propane, benzene, ethanol, methanol, and Freon. Mixtures of two or more elements and/or compounds mixed together to alter melting temperature or other physical characteristics can also be used as the refrigerant; e.g. Water+NaCl→Brine, Oxygen+Nitrogen→Slushed/Solid Air, Ethane+Propane.

Any substance or compound can be used as the refrigerant for this freezing method as long as it can rapidly absorb heat from liquid droplets by its phase change from solid to partially solidified to liquid. The melting temperature of the refrigerant must be lower than the liquid droplet freezing temperature, and the heat of fusion absorbed by the refrigerant (along with some additional heat absorbed by the liquefied refrigerant in some cases) must be greater than the heat of fusion released by the freezing liquid droplets.

A variation of this freezing method involves the use of sublimating compounds as the refrigerant. The phase change from solid to liquid is the basic process for absorption of heat from freezing droplets, but the phase change from solid to gas of the refrigerant can also be used. An example is spraying nebulized liquid droplets directly onto or into the surface of solid carbon dioxide. A disadvantage of this method is the generation of an insulating gas layer around the droplets, which may slow the rate of freezing. This disadvantage can be overcome using devices that rapidly drive the liquid droplets into the solid refrigerant in order to maintain direct contact between their surfaces.

The production of solid or slushed refrigerants, especially in the cryogenic temperature range, requires mechanical means or a secondary refrigerant. The mechanical means may be in the form of a refrigeration means or a vacuum chamber. Liquid refrigerant is placed in a vacuum chamber and placed under partial vacuum to achieve at least partial solidification of the refrigerant. The secondary refrigerant can be any heat-absorbing substance held at a temperature lower than the freezing point of the primary refrigerant. A secondary refrigerant is used to freeze the primary refrigerant into a solid or slushed state either by direct contact or by indirect contact through a container. Freezing of the primary refrigerant may be a one-time single event, or can occur as a repetitive or continuous renewal process. Selection of appropriate primary and secondary refrigerants results in production of an optimal slushed primary refrigerant or may be used to change the working temperature of the primary solid refrigerant to maximize liquid droplet freezing rates. For example, frozen argon held at the temperature of liquid helium will absorb much more heat more rapidly from liquid droplets than frozen argon held at liquid nitrogen temperature. Because of the wide range of freezing temperatures for various elemental, compound and organic refrigerants, numerous combinations of primary and secondary refrigerants are possible. The secondary refrigerant for one rapid-freezing application can be used as a primary refrigerant for another application. Examples of primary and secondary refrigerants are provided in Table 1.

23 is positioned inside a housing 25 half-filled with liquid primary refrigerant such that the drum 23 is partially submerged in the primary refrigerant. The apparatus further comprises a series of nebulizers 27–29 positioned over the exposed surface of the drum 23. As the drum 23 rotates, the secondary refrigerant inside causes a layer of frozen primary refrigerant to form on the exposed surface. Sample is sprayed from nebulizers 27–29 onto the frozen primary refrigerant on the surface of the drum 23. As the drum 23 rotates, the frozen sample floats off into the liquid primary refrigerant. The frozen sample is collected by skimming, sedimentation, or filtration of the liquid primary refrigerant, depending on the density of the frozen sample.

Another embodiment of the invention is illustrated in FIG. 4. Housing 30 has a sloped upper surface comprising grooves 31. The end walls of the grooves have openings 32 connected to a pipe 33 at the upper end, and to a trough 34 at the lower end. The housing 30 is hollow with inlet 35 and outlet 36 ports for circulating liquid secondary refrigerant through the housing 30. The device further comprises multiple nebulizers 37, one positioned over each groove. Liquid primary refrigerant is transported from the pipe 33 through the openings 32, down the grooves 31 where it freezes due to the liquid secondary refrigerant circulating through the

TABLE 1

| | | | PRIMARY REFRIGERANT | | | | | | | | | | | | | |
|---|---|---|---|---|---|---|---|---|---|---|---|---|---|---|---|---|
| SECONDARY REFRIGERANT | Melting Point ° C. | Melting Point ° C. | Hydrogen | Neon | Oxygen | Nitrogen | Propane | Argon | Butene-1 | Ethane | Krypton | Ethanol | Xenon | Mercury | Water | Gallium |
| Helium | −272.20 | −268.90 | ○ | ○ | X | X | X | X | X | X | X | X | X | X | X | X |
| Hydrogen | −259.14 | −252.87 | | X | X | X | X | X | X | X | X | X | X | X | X | X |
| Neon | −248.67 | −246.05 | | | X | X | X | X | X | X | X | X | X | X | X | X |
| Oxygen | −218.40 | −182.96 | | | | ○ | ○ | ○ | ○ | ○ | X | X | X | X | X | X |
| Nitrogen | −209.86 | −195.80 | | | | | X | X | X | X | X | X | X | X | X | X |
| Propane | −189.69 | −42.07 | | | | | | | ○ | ○ | ○ | ○ | ○ | X | X | X |
| Argon | −189.20 | −185.70 | | | | | | | | — | — | X | X | X | X | X |
| Butene-1 | −185.35 | −6.30 | | | | | | | | — | — | — | — | ○ | X | X |
| Ethane | −183.30 | −88.63 | | | | | | | | | ○ | ○ | ○ | X | X | X |
| Krypton | −156.60 | −152.30 | | | | | | | | | | X | X | X | X | X |
| Ethanol | −117.30 | 78.5 | | | | | | | | | | | — | — | — | — |
| Xenon | −111.90 | −107.10 | | | | | | | | | | | | X | X | X |
| Mercury | −38.87 | 356.58 | | | | | | | | | | | | | X | X |
| Water | 0.00 | 100.00 | | | | | | | | | | | | | | ○ |
| Gallium | 29.78 | 2403.0 | | | | | | | | | | | | | | |

X = primary refrigerant freezes in secondary refrigerant
○ = primary refrigerant freezes in chilled secondary retrigerant
— = primary refrigerant barely freezes in chilled secondary refergerant Referring to FIG. 2, the hyper-rapid freezing apparatus is generally referred to at 14. It comprises a nebulizer 15 positioned inside a nebulizer column 16 which fits into an opening 21 in a hollow sphere 17 containing argon. The sphere is placed into a container 19 of liquid nitrogen. The liquid nitrogen causes the argon inside the sphere to freeze along the walls. A sample is delivered to the nebulizer 15 via the nebulizer column 16 and sprayed onto the solid argon on the inner walls of the sphere 17. The frozen sample accumulates in the liquid argon at the bottom of the sphere 17 and is collected by removing the nebulizer column 16 from the sphere 17 and pouring out the liquid argon. Alternatively, the sphere 17 can be used for storing the frozen sample by removing the nebulizer column 16 and plugging the opening 21.

An embodiment of the invention is illustrated in FIG. 3. The hyper-rapid freezing apparatus 22 comprises a rotating drum 23 filled with liquid secondary refrigerant. The drum housing 30. Sample is sprayed onto the frozen primary refrigerant in the grooves, causing the refrigerant to melt and flow into the trough 34.

A further embodiment of the invention is illustrated in FIG. 5. Housing 38 is divided into two sections, one filled with liquid secondary refrigerant, and the other partially filled with liquid primary refrigerant. A rotating metal disk 39 is positioned half in one section and half in the other section such that the disk is in contact with both the primary and secondary refrigerants. The secondary refrigerant cools the metal disk causing a layer of frozen primary refrigerant to form on the exposed surface of the disk. The device further comprises one or more nebulizers 40 positioned in the housing section containing primary refrigerant such that sample is sprayed onto the frozen primary refrigerant coating the exposed portion of the disk.

Another embodiment of the invention is illustrated in FIG. 6. The device comprises a vertical cylindrical pipe 41 within a larger cylindrical container 42. The container 42 comprises a lower section filled with liquid secondary refrigerant and an upper section. The pipe is positioned such that the top opening 43 is in the upper section of the cylindrical container 42 and the bottom opening 44 is below the lower section of the cylindrical container. Insulation 45 surrounds the cylindrical container. A conduit 46 connected to the lower section of the cylindrical container 42 transports the liquid secondary refrigerant. A nebulizer 47 is positioned over the top opening 43 in the pipe 41. Liquid primary refrigerant is forced under pressure up into the pipe. The primary refrigerant freezes as it passes through the lower section of the cylindrical container, and is extruded out of the top opening of the pipe. Sample is sprayed onto the extruded primary refrigerant.

Primary refrigerants in slushed or solid forms can be produced (frozen) or held at working temperatures by mechanical refrigeration devices. Although generally more expensive than the use of secondary refrigerants, the mechanical devices allow greater control of the working temperature of the primary refrigerant. An embodiment of the invention utilizing mechanical refrigeration is illustrated in FIG. 7. The device comprises a source of mechanical refrigeration 48 connected to one or more containers of primary refrigerant 49. Depending on the temperature achieved by the mechanical refrigeration source, the refrigerant will be either in the slushed or solid state. A nebulizer 50 is positioned above the container of refrigerant.

The physical size of the sample liquid droplets to be frozen has a significant influence on the freezing rate achieved by this method. In general, the smaller the liquid droplet, the faster it will freeze. Nebulizer type and control can be used to obtain optimal drop or droplet sizes for individual applications of the freezing method.

A large number of nebulizing, atomizing and vaporizing devices using different operating principles are available, any of which can be used to produce liquid droplets in a variety of sizes and rates for this freezing process. These include spray nozzles, pressurized small apertures, gas driven nozzles, fine screen methods, ultrasonic devices, and drip nozzles. Selection of an appropriate device depends on the specific freezing application and desired drop size, e.g. biological or fragile specimens may be damaged by some nebulizers and may require more gentle types such as glass-fret or fine screen nebulizers.

A flow cytometer can also be used for producing liquid droplets of specific sizes. A flow cytometer can be used to achieve individual drops containing a single cell, or specific numbers of cells. The amount of fluid per cell can also be controlled to achieve optimal freezing conditions which provide for optimal viability upon thawing. The flow cytometer may be communicatively coupled to a container containing a suspension of biological material to be frozen.

The liquid droplet heat of fusion and droplet-to-primary refrigerant temperature gradient are the factors determining the total amount of heat to be removed from the droplet to achieve complete freezing. The rate of freezing depends on these factors and the specific heat and the thermoconductivity of the droplet and the primary refrigerant. The freezing rate can be altered by lowering the initial temperature of the droplets, or by changing the heat of fusion by adding solutes. For example, most biological specimens in liquid solutions can be precooled to within a few degrees above the freezing point without significant damage, which would reduce the total amount of heat to be removed from the liquid droplets and increase the rate of freezing at the time of contact with the primary refrigerant.

Cryopreservatives may be added to the liquid samples to improve the survival of biological or other specimens. For freezing rates that do not achieve vitrification of the sample, ice crystal or frozen crystal sizes can be minimized by the addition of a cryopreservative.

The velocity of droplet impact into the primary refrigerant has a significant influence on the freezing rate of the droplet. A slow approach and slow impact of the droplet will result in slower freezing rates with more crystal content or larger crystal sizes, or even result in prefreezing of the droplet before impact with the primary refrigerant as the droplet passes through the temperature gradient above the surface of the refrigerant. Increasing the velocity of the droplets before impact will result in more rapid freezing rates, and this can be achieved by increasing the pressure of spray or gas nebulizers, or by decreasing the distance between the nebulizer and the primary refrigerant. Fragile specimens or biological specimens may be damaged by the high fluid shear forces of high pressure nebulizers, so increasing the velocity of these nebulized specimen droplets would require low pressure/velocity nebulization followed by acceleration of the droplets using injection of a gas carrier into the nebulizer stream or by centrifugation of the stream. A high humidity or water saturated atmosphere, and very fast spray velocities can be used to minimize evaporation of the sample drop. Rapid spray velocities limit the amount of time for evaporation to occur, and increase the temperature gradient near the refrigerant surface, reducing the chance of precooling the sample. Because evaporation of a liquid droplet is increased on the forward side when it is sprayed into a still atmosphere, further refinements of the designs involved spraying nebulized droplets into a stream of humidified or saturated air or other gas moving in the same direction at about the same velocity, with the air stream and nebulized stream directed onto the refrigerant surface.

Direct injection of nebulized droplets into the solid or slushed primary refrigerant can maximize the freezing rate for some applications. This can be achieved by inserting the aperture of the pressure or spray nebulizer into the refrigerant slush or onto a solid. As the liquid encounters the refrigerant, it breaks up into small droplets, and the chaotic flow of the droplets through the slush or solid increases the transfer of heat from the droplets resulting in very high freezing rates. Nebulizer apertures may remain stationary when inserted into slushed refrigerants, but optimal results from solid refrigerants may require moving the nebulizer aperture along the surface of the frozen refrigerant.

An embodiment of this variation of the invention is illustrated in FIG. 8. The device comprises a centrifuge 51 with paddles 52 holding solid primary refrigerant 53 connected to the rotor 54. One or more nebulizers 55 are positioned in the walls of the centrifuge such that sample delivered to the nebulizers is sprayed onto the solid refrigerant as the rotor turns.

A variation of the embodiment utilizing a centrifuge is illustrated in FIG. 9. A nebulizer 56 is positioned over a centrifuge 57 containing solid primary refrigerant. Sample is sprayed from the nebulizer onto the spinning surface of refrigerant and the frozen droplets of sample move to the outer edge, leaving the center of solid refrigerant open to receive more sample.

Another variation of the embodiment utilizing a centrifuge is illustrated in FIG. 10. A column 58 attached to a rotating head 59 comprising multiple horizontal nebulizers 60 is positioned over a cylindrical container 61 with solid refrigerant coating the walls. Sample is delivered to the nebulizers through the column and sprayed onto the solid refrigerant coating the walls of the container as the head rotates.

Figure 11:
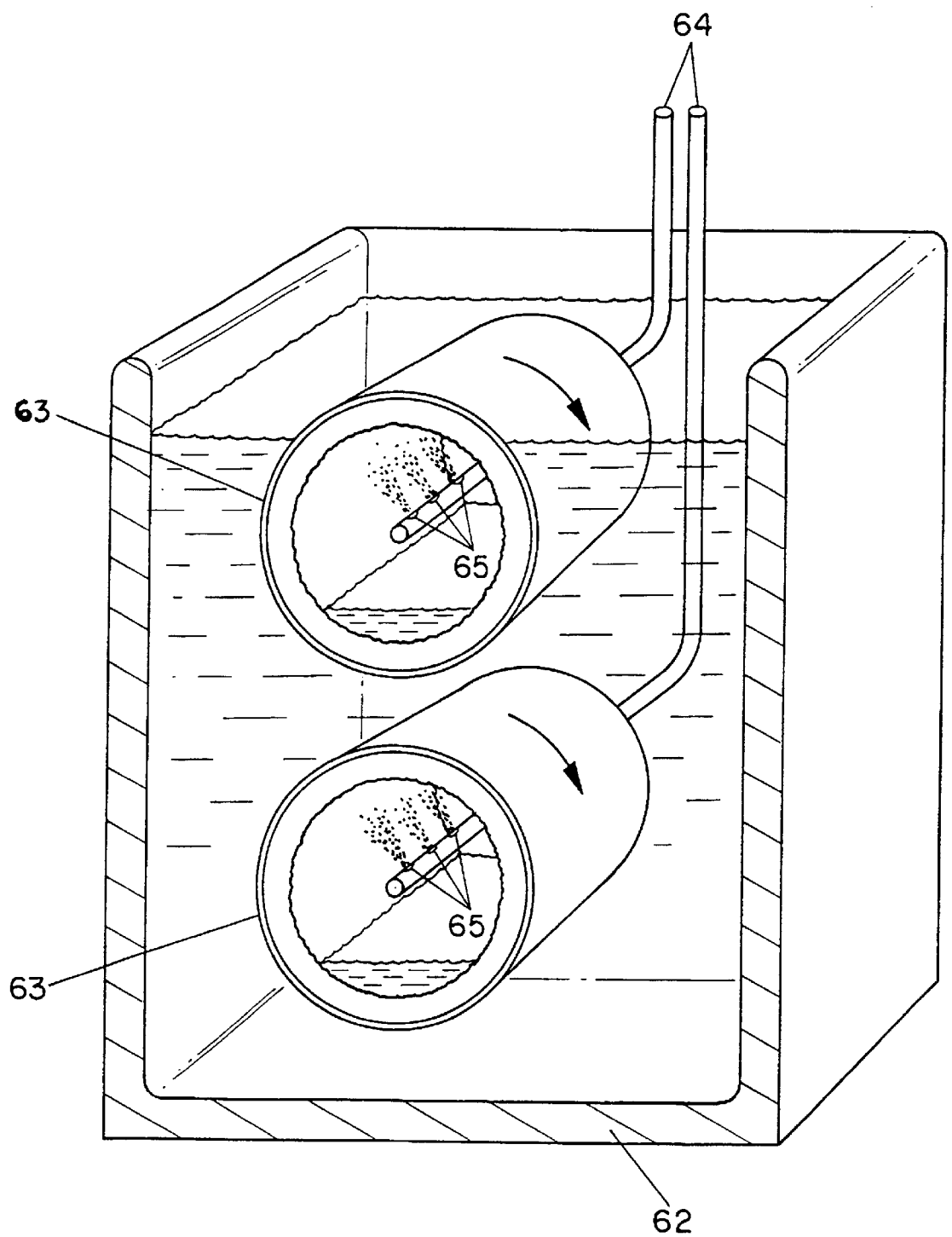
FIG. 11 is a cross-sectional view of a device for hyper-rapid freezing with multiple sample freezing chambers.
Figure 13:
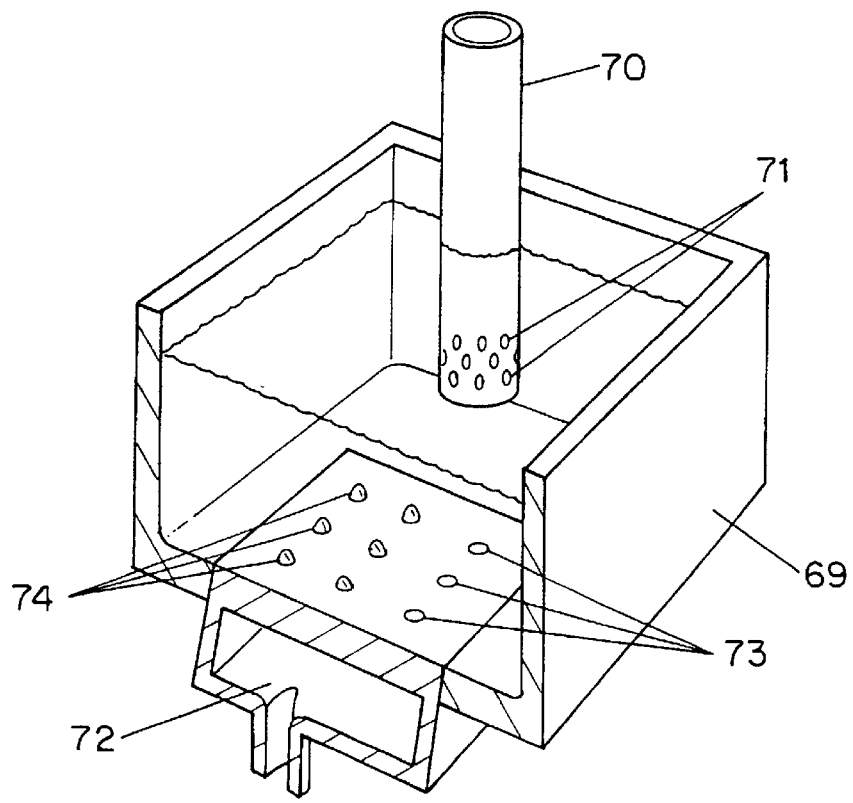
FIG. 13 is a cross-sectional view of a device for hyper-rapid freezing utilizing direct injection of sample into partially solidified refrigerant.
Figure 14:
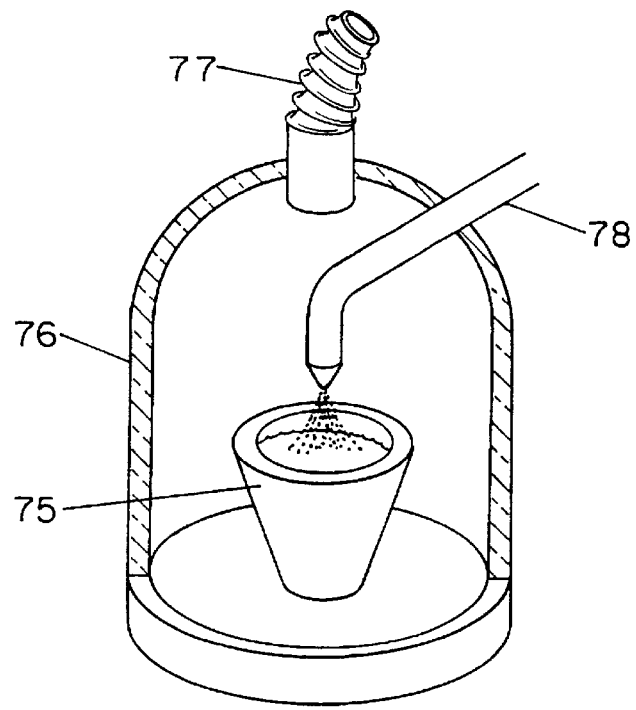
FIG. 14 is a perspective view of a vacuum chamber for evaporative cooling of refrigerant.

A further embodiment of the invention is illustrated in FIG. 11. The device comprises a housing 62 filled with liquid secondary refrigerant. One or more hollow rotating cylinders 63 are positioned such that they are submerged in the liquid secondary refrigerant. Inlet tubes 64 for sample transfer are connected to respective cylinders. Nebulizers 65 are positioned on the tubes inside the cylinders to deliver sample to the inside walls of the cylinders. Liquid primary refrigerant is placed inside the cylinders. As the cylinders rotate, the primary refrigerant freezes on the walls. Sample sprayed onto the cylinder wall freezes and drops into the remaining liquid refrigerant at the bottom of the rotating cylinder. When the cylinders are removed from the housing they may be used for storing the frozen sample.

An embodiment of the invention utilizing direct injection of sample onto solid refrigerant is illustrated in FIG. 12. The device comprises a rotating cylindrical receptacle 66 with solid refrigerant coating the inner walls, and a sample delivery tube 67 with an injection aperture 68 at the end. The delivery tube is positioned such that the injection aperture is in close proximity to the solid refrigerant coating the receptacle walls.

Another embodiment of the direct injection apparatus is illustrated in FIG. 13. The device comprises a receptacle 69 holding slushed refrigerant. A cylinder 70 with small injection apertures 71 located at one end is positioned in the receptacle such that the injection apertures are submerged in the slushed refrigerant. Pressurized sample is delivered through the injection apertures in the cylinder into the slushed refrigerant. Alternatively, the device may comprise an injection apparatus 72 connected to the bottom of the receptacle 69. In this embodiment, the receptacle has small injection apertures 73 in the bottom. Sample is injected into the slushed refrigerant in the receptacle by means of nebulizer jets 74 in the injection apparatus.

One of the advantages of this rapid freezing method is the very high freezing rates achieved at atmospheric pressure. However, some special applications may be optimized by increasing the pressure at the droplet- refrigerant interface. High pressure can be used to produce a solidified or slushed primary refrigerant (i.e. liquid helium) or increase the thermoconductivity of the refrigerant or droplets. Enclosing the basic apparatus (nebulizer and primary refrigerant) in a pressure chamber would be a typical method to achieve this process. Other special applications may require reducing the pressure below atmospheric, and a similar vacuum chamber would be used in these cases. A vacuum chamber for producing solid or slushed primary refrigerant is shown in FIG. 14. A container 75 of liquid primary refrigerant is placed inside a vacuum chamber 76 attached to a vacuum pump 77. A nebulizer 78 is positioned over the container 75 of primary refrigerant. The low pressure conditions created by the vacuum pump cause evaporative cooling of the primary refrigerant.

Most of the individual methods for rapid freezing of nebulized liquids are limited by the output of the nebulizer. The rate that the liquid sample is frozen is determined by the maximum flow achieved through the nebulizer, or in some instances, the rate of production of delivery of the primary refrigerant. The rate of production of frozen particles by any unit (made up of a nebulizer and primary refrigerant delivery) is limited to an inherent maximum. In order to increase the production of frozen particles, the number of freezing units can be increased, and high outputs can be achieved by running a large number of identical freezing units in parallel. In general, the output of the nebulizer is the limiting component of each unit, so a typical system would be made up of several nebulizers sharing a central primary refrigerant delivery (or possibly several parallel refrigerant delivery units).

The process for extremely rapid freezing of liquids has a large number of industrial, medical, biological, and research applications. Industrial applications of this process include freezing liquid compounds with minimal chemical damage to the compound, lyophilization with high recovery rates, and creation of small crystal or amorphous solids with special transparency, electrical, thermoconductive, or other physical properties. Medical and biological applications include cryopreservation of cells, especially oocytes, and tissue with minimal ice crystal or osmotic damage, or production of minimal-damage samples for microscopic or electron microscopic examination. Research applications include production of vitreous ice, and freeze-stopping chemical or biological reactions. In order to achieve the extremely rapid cooling rates required for these applications, heat must be removed very quickly from the liquid samples. Barriers to rapid heat extraction from the liquids, such as insulating gas envelopes or large thermoconductive distances across the liquid, must be eliminated or minimized. These barriers are overcome or minimized by the freezing process of the instant invention. The insulating gas envelope around a liquid sample immersed in a liquid refrigerant is replaced by a high thermoconductive interface with a solid or slushed refrigerant. Heat extracted from the liquid sample is used to melt the refrigerant into a liquid instead of boiling it into an insulating gas layer. The heat extraction barrier resulting from large thermoconductive distances across the liquid sample is minimized simply by reducing the liquid sample to small drops, droplets, or a nebulized mist. Reducing the liquid sample to droplets or mist also dramatically increases the surface area (i.e. the heat flux interface available) of the liquid, further increasing the rate of cooling.

The simplest version of this process involves nebulizing a liquid sample, then rapidly driving the nebulized stream onto or into a solid or slushed refrigerant. The nebulized liquid sample is very rapidly frozen into tiny solid particles which can then be easily collected and stored.

Beneficial features of this freezing process include use of the refrigerant's solid-to-liquid phase change, very rapid freezing at a large scale, ease of sample separation and storage, low-cost materials, simplicity, and variable freezing rates, along with inert nonreactive components for most applications. These features solve or improve on the limitations imposed by current prior-art freezing methods.

The solid-to-liquid phase change of the refrigerant bathes the sample in a liquid for faster heat transfer (higher thermoconductivity) instead of a boiled gas envelope with lower thermoconductivity which occurs when liquid refrigerants are used. This concept is general, encompassing any cryogenic frozen or slushed gas as the refrigerant. Frozen gases can be held at any temperature below the freezing point, and slushed gases can be held at the fusion temperature corresponding to any ambient or applied pressure. Samples to be frozen are typically liquid at any concentration, but may also be non-liquid as long as they have the capacity to be frozen by the solid or slushed refrigerant selected. Non-liquid samples include metals, oil-based organic compounds, lipids, plastics, and silicone substances, or others not limited to these categories.

Samples can be immersed or applied to the refrigerant in the form of thin films, in vials, tubes, or other containers, or as drops, sprays, droplets, or in nebulized or atomized forms. Optimal hyper-rapid freezing results are obtained with the optimal combination of refrigerant type (gas element or compound), refrigerant phase (solid or slushed), refrigerant temperature, sample type (liquid, non-liquid), sample phase (liquid, nebulized, atomized, vapor), sample temperature, and the method of application (direct spray, drop, air stream). Vitrification of water or other liquids directly from the vapor phase is achieved by blowing a gas saturated with the liquid vapor directly onto a solidified gas surface (example—air saturated by water vapor).

A method was devised to produce a liquid-solid refrigerant slush. The melting point of nitrogen is −209.86° C., which is the slush temperature at one atmosphere pressure. A refrigeration method or colder substance would be needed to reduce the commercially available liquid nitrogen (at about −195.8° C.) temperature to the freezing point.

Review of the physical properties of gases revealed that argon, krypton, and xenon have freezing points above that of liquid nitrogen. These gases can be frozen in liquid nitrogen, and samples or substances to be rapidly frozen can be placed in physical contact with the solidified or slushed gas produced. The solid gas used for initial studies was argon (freezing point=−189.2° C.). Because it is a noble gas, it is non-reactive and relatively safe to handle.

Solid/slushed gas technology was used to vitrify water and freeze biological specimens. Cryostats were filled with liquid nitrogen and liquid argon from Liquid-Air Corp in Phoenix, Ariz. Liquid argon was poured into Pyrex test tubes (10–12 cc), which were then lowered into a Dewer flask containing liquid nitrogen. The argon sample froze solid in 1 to 2 minutes, and the solid cylinder of argon was dumped onto a Styrofoam tray. A silver wire loop 1 cm in diameter was dipped into distilled water, then rapidly plunged manually into the solid argon. The water film shattered into several droplets of instantly frozen ice. Initial biological specimen studies were performed using 2-cell mouse embryos. The same silver wire loops were clipped into culture media containing the embryos, and a liquid film of media containing at least one embryo was obtained in the loop. This was rapidly and manually plunged into solid argon cylinders, achieving hyper-rapid freezing in the form of small shattered droplets less than 1 mm diameter. A total of eight mouse embryos were frozen in this manner, and microscopic inspection of the embryos upon thawing revealed that four had zona fracture and cell membrane rupture damage, and the other four were intact and visually undamaged.

A container for the liquid or biological sample is unnecessary. Small bare droplets of the sample can be dropped directly into the cryogenic slush or onto the solidified gas. Chemical contamination or damage to the sample does not occur, especially if a noble gas such as argon is used for the refrigerant. The small shattered film droplets from the first experiments demonstrated the feasibility of this innovation, so technical designs for dropping small liquid drops of protein or biological samples onto solid cryogenic gases or slushes were made, with the limiting factor of acceleration of small drops by gravity through air. Very small drops arrive more slowly to the refrigerant surface, passing through a slower temperature gradient and increasing the freezing time (and ice crystal size). In order to overcome this limitation, a nebulizer was used to produce a fine spray of liquid sample with extremely small droplet sizes, then accelerating the fine spray rapidly into the slush or solid refrigerant surface.

Vitrification of water is expected because droplet diameters can be less than the water film thickness achieved in the examples in the reference publications, in which vitrification was not achieved. However, the smaller the droplet the more susceptible it is to the temperature gradient near the refrigerant surface. If the surface is not approached rapidly enough, the small droplet will pre-freeze slowly in the air before making contact with the surface, resulting in larger ice crystal formation. The advantages of the solid-to-liquid phase change in hyper-rapid freezing applies only to droplets that penetrate the surface of a solidified gas or slush in the liquid state. Nebulized samples should therefore be sprayed or driven onto the refrigerant surface very rapidly.

Another concern regarding very small nebulized droplets is susceptibility to rapid evaporation. The increased surface to volume ratio of small droplets allows a rapid phase change from liquid to gas, so the droplet could evaporate entirely before it reaches the refrigerant surface.

The improved designs of the nebulizer freezing method include use of a high humidity or water saturated atmosphere, and very fast spray velocities to maximize the life-span of the droplets. Rapid spray velocities limit the amount of time for evaporation to occur, and increase the temperature gradient near the refrigerant surface, reducing the chance of precooling the sample. Evaporation of a liquid droplet is increased on the forward side when it is sprayed into a still atmosphere. Therefore, further refinements of the designs involve spraying nebulized droplets into a stream of air moving in the same direction at about the same velocity, with the air stream and nebulized stream directed onto the refrigerant surface.

Some fragile protein or biological samples may be damaged or denatured by the high fluid shear forces of the nebulizer. Low initial nebulizer spray velocities and high air stream velocity can be used to accelerate the slow droplet to high surface-impact speeds, while protecting the sample from high fluid shear forces.

A typical technical design is a hollow metal sphere filled with liquid argon, then immersed in liquid nitrogen (FIG. 2). Once argon freezes onto the inner rim of the sphere, the container is withdrawn and the center core of remaining liquid argon is poured out through a hole in the top of the container, leaving a shell of solid argon frozen to the inner surface. A nebulizer head is then passed through the hole, to the center of the sphere. The liquid sample is sprayed onto the solid argon, rapidly freezing the nebulized droplets into tiny ice spheres. Sample fusion heat melts the solid argon, and the liquid argon then flows on the bottom of the sphere, collecting into a pool and washing the frozen sample droplets to a central location. The frozen sample consists of a large number of tiny ice particles with undamaged protein, biological, or other substances imbedded inside. These can be recovered, or left and stored in the liquid argon, which is now used as a storage refrigerant.

Other technical designs involve spraying nebulized samples onto an argon slush or onto sheets of frozen argon. A mass production design uses a hollow metal cylinder filled with continuously circulating liquid nitrogen, with the horizontal cylinder half submerged in a pool of liquid argon (FIG. 3). Slow rotation of the cylinder allows a shell of frozen argon to coat the outside surface, upon which a continuous spray of liquid nebulized sample is driven. Frozen sample droplets in liquid argon then flow into the pool of liquid argon to be collected.

Hyper-rapid freezing of liquids (or vapors) by nebulized droplet contact with solidified or slushed cryogenic gases has several features and advantages. These novel features include:

The solid-to-liquid phase change of the cryogenic "gas" refrigerant allows a high density liquid medium to surround the freezing sample droplets. A liquid medium has a much higher thermoconductivity than a low density gas medium, so heat is transferred more rapidly and efficiently out of the sample droplet, resulting in a higher freezing rate than samples surrounded by a liquid-to-gas refrigerant phase change. The cryogenic refrigerant solid-to-liquid phase change rapidly absorbs heat and efficiently transfers heat from the liquid or vapor substance being frozen. The liquid substance to be frozen makes direct contact with the surface of the refrigerant, typically being completely or partially surrounded by the liquefied refrigerant, thus increasing the surface area available for heat flux into the refrigerating solid or slush and out of the freezing sample. Freezing rates are dramatically increased by the extremely high surface to volume ratio of small droplets in the nebulized sample, or by the direct application of a vaporized sample. Rapid heat flux is further increased by direct contact between the refrigerant and the liquid sample. Freezing rates are maximized without an intervening layer of another substance, such as a container or conduit wall.

The solid-to-liquid refrigerant phase change coupled to the high surface-to-volume ratio of nebulized droplets produces extremely rapid freezing rates, which allows minimal or no ice crystal formation and minimal osmotic damage to liquid biological samples. The hyper-rapid freezing method is easily expandable to allow large scale freezing of large volumes of liquid samples. Devices designed to use this process can be readily scaled up for larger sample volumes because of the continuous nature of the process, and the adaptability of the process to the use of multiple parallel basic devices.

The hyper-rapid freezing process can be applied in a continuous manner and is easily adapted to economies of scale by the use of multiple parallel devices, resulting in low costs for small volumes or large volumes of frozen samples. The surface of solidified gas refrigerant can be continuously renewed by systems using rotating drums, extruded plugs, etc., and a slushed gas refrigerant surface can be renewed by continuous flow. These systems produce a constantly-available fresh surface of refrigerant to allow continuous freezing of a steady stream of nebulized samples. Large scale freezing is further enhanced by the low cost of some refrigerant raw materials (e.g. liquid nitrogen and liquid argon).

Nebulized sample particles frozen using this method are easily recovered because they remain suspended in the liquefied primary refrigerant at the end of the freezing process. The primary refrigerant liquefies after absorbing heat from the sample, then washes the frozen sample droplets away from the active freezing contact site. Depending on the difference in density between the frozen sample particles and the liquefied refrigerant, the sample particles can be recovered 1) by gravity at the bottom of the refrigerant vessel, 2) by skimming or overflow after floating to the refrigerant surface, or 3) by filtration if suspended within the refrigerant. The ease of sample recovery is a distinct advantage over other prior-art methods, which require scraping frozen samples off cold metal surfaces, removing samples from porous or thin film plates, detaching samples from metal grids, or unsealing samples from tubes or metal canisters. Short or long-term storage of frozen nebulized samples is also greatly simplified by this freezing method, again because the sample remains within the liquefied primary refrigerant after freezing. As outlined above, the primary refrigerant is generally nonreactive and nontoxic, typically liquid nitrogen or a liquefied noble gas, so the frozen sample is subjected to no long-term adverse effects if it remains suspended in the primary refrigerant for storage. An additional advantage is that the sample remains at its freezing temperature indefinitely because there is no need to transfer to another container or medium for storage, so the risk of heating the sample above one of its glass or crystalline transition temperatures is minimized.

Solid or slushed cryogenic "gas" refrigerants used in this method may be noble gases (He, Ne, Ar, etc.) or common industrial cryogens (nitrogen) which are generally chemically nonreactive and nontoxic. This is especially useful when freezing organic or biological materials, or living cells, because the freezing samples come into direct contact with the refrigerants, and some of the refrigerant substance is expected to diffuse into the frozen samples. The use of nonreactive and nontoxic refrigerants is a significant advantage over methods that use organic solvents such as ethane, propane, and butane as liquid refrigerants. Frozen samples are heavily contaminated by these organic solvents, which poison the sample or require removal (usually by a less-toxic organic solvent). Use of noble gases, or in some instances nitrogen, is especially useful for "time stopping" experiments using samples of actively reacting chemicals.

Primary (solid-to-liquid phase) refrigerants and secondary refrigerants (those used to initially freeze the primary refrigerants) are typically inexpensive atmospheric or industrial cryogenic liquefied gases currently mass-produced by efficient industries. They include liquid nitrogen, liquid argon, and liquid helium, and can be extended to more exotic refrigerants such as liquid hydrogen, liquid neon, liquid oxygen, alcohol, or even chilled metals such as mercury. Most of the refrigerants are abundant, easy to ship and handle, and are inert, reducing the cost of purchasing or using the primary raw materials of the process. Waste products generated by the process, typically atmospheric gases or helium, are simply vented or recycled, or for hydrogen, simply burned to produce water vapor, so disposal costs of waste products are minimal or absent. The low cost of operation and the wide availability of raw materials makes this process less expensive than other hyper-rapid freezing methods. Most nebulizers are inexpensive pressure spray nozzles or common ultrasonic commercial devices. These relatively inexpensive items represent a significant cost advantage over currently used rapid freezing devices containing high pressure vessels, programmable electronic variable rate cooling systems, mechanical or electromagnetic sample plungers, or elaborate chemical preparation of samples. Another cost advantage of this freezing process is the absence of organic solvent or waste disposal—the refrigerants are simply recycled or are vented off into the atmosphere.

This freezing process has a minimal number of working components: 1. a sample storage and delivery system, 2. nebulizer or atomizer, 3. primary frozen or slushed refrigerant, 4. secondary refrigerant, 5. sample recovery system, and 6. appropriate insulation. The number of moving parts is also minimized, with the simplest configuration consisting of a moving stream of nebulized sample droplets directed against a stationary primary refrigerant. The process simply requires that a high velocity stream of liquid be directed onto a surface of solid or slushed cryogenic gas. More complicated procedures used in currently available freezing methods, such as programmable freezing curves, elaborate sample preparations, or ice crystal seeding steps, are avoided. Because the process is simple, equipment costs are reduced, along with equipment failure rates and maintenance requirements. More complete automation is permitted by the simplicity of the process, and the high speed inherent in freezing single samples allows rapid production and delivery compared to other currently used methods.

Basic control of this freezing process is easily accomplished by simple adjustments of a few inherent variables. The rate of freezing is determined by the temperature gradient applied to the nebulized droplet, and this is easily controlled by changing the velocity of the nebulized spray onto the primary refrigerant, the temperature of the primary refrigerant, or the composition of the primary refrigerant and its associated properties of melting point, thermoconductivity, and purity. Spray impact velocity can also be easily controlled by changing the distance between the nebulizer and the primary refrigerant, as the nebulized stream will usually lose velocity with increasing distance from the nebulizer. A notable subtype of this control is using a nebulizer-refrigerant distance of zero, i.e. spraying the nebulized droplets directly into the slushed or solid primary refrigerant, which would have the additional benefit of increasing chaotic flow and heat transfer in the nebulized stream. Control of freezing rate and heat transfer is also easily achieved by changing the size of the nebulized droplets, and thus, their surface-to-volume ratio, by using different types of nebulizers or atomizers, changing nebulizer aperture size, or altering the nebulizer fluid pressure. Addition of cryopreservative solutions to sample fluids is an optional method to reduce ice crystal size or formation. Various cryopreservatives may be used, including dimethyl sulfoxide (DMSO), dextran, sucrose, 1,2 propanediol, glycerol, sorbitol, fructose, trehalose, raffinose, hydroxyethyl starch, propylene glycol, 2–3 butane diol, polyvinylpyrrolidone (PVP), proline, human serum albumin, and combinations thereof. Easy control of the freezing parameters using this method represents a distinct advantage over other prior-art methods.

Different rates of freezing are required to obtain the desired outcome for various liquid samples, depending on the solvent, concentration, requirement for vitrification, requirement for size of ice crystals, or nebulization limitations. The freezing rate generated by the process can be easily adjusted to satisfy these requirements by selecting the proper primary refrigerant (e.g. solid nitrogen vs. solid argon) or secondary refrigerant (e.g. liquid helium to freeze argon or alcohol), or by changing the size of the nebulized sample droplets. Other adjustable variables that change freezing rates include the velocity of the nebulized stream, and the use of a solid vs. slushed refrigerant. All of these adjustments can be designed into a single freezing device, which could then be used to freeze a wide variety of substances and samples with different freezing rates.

The process allows easy interchange or replacement of its basic components—primary and secondary refrigerants and nebulizers. Drainage and replenishment of refrigerants is accomplished by pumps or gravity fill, and waste gases are removed by vents. Nebulizers, atomizers, flow cytometers and vapor generators can be easily changed to produce the desired spray volume, rate, or droplet size.

EXAMPLE 1

A rapid stream of nebulized water droplets was achieved. The droplets were hyper-rapidly frozen by directing the stream onto the surface of frozen argon. The frozen droplets were collected in the liquid primary refrigerant.

Equipment

1 Styrofoam ice chest (1 gallon)
nebulizer—ultrasonic
box fan (5 inch) 120 volt 60 Hz
1 Styrofoam platter with concave hemispheric surface
Pyrex glass test tubes—red-toe large 20 ml
open mouth Dewer flask
1 vacuum thermos bottle
1 foam thermos cup (250 ml)
liquid nitrogen
liquid argon A ½ inch diameter hole was drilled through the ice chest wall ½ way up the side to form a side port. A 4½ inch square was cut out of one end of the Styrofoam ice chest lid and 4 holes (½ inch) were drilled into the lid at the opposite end. The box fan was embedded in the square hole and taped in place, and the fan lead wires were soldered to a transected electrical extension cord. A tape strap was placed over the 4 holes in the lid, with control of forced air achieved by removal of tape from 0, 1, 2, 3, or all 4 holes. The ultrasonic nebulizer was placed under 4 inches of water inside the Styrofoam ice chest.

The fan and ultrasonic nebulizer were turned on, achieving a well-controlled very rapid stream of nebulized mist through the side port of the ice chest. The mist stream direction was easily controlled by placing a glass pipette through the side port.

Six Pyrex glass test tubes were precooled in liquid nitrogen, then ¾ filled with liquid argon (approximately 12 cc–15 cc). The test tubes were partially immersed in liquid nitrogen for 10 minutes, and 90% to 100% of the argon was frozen solid in each tube. The Styrofoam working tray contained an approximate 8 inch hemispheric depression. The depression was precooled with liquid nitrogen for 2 minutes. All liquid nitrogen was then poured out of the working tray, and the six test tubes of frozen argon were then emptied into the working tray depression. Solid frozen argon was in the form of transparent cylinders of approximately 12 cc initial volume each.

The Styrofoam working tray was tilted approximately 30°, allowing the frozen argon cylinders to remain in the middle of the depression, and melted argon flowed off center to a collection area at the lowest point. The stream of nebulized mist from the side port of the ice chest was then directed against the frozen argon cylinders using the glass pipette for stream control. The movement of the nebulized mist stream was rapid (estimated 1 to 1½ meters/sec), and distance of stream pipette to frozen argon surface was 10 cm.

Nebulized water droplets froze on impact with solid argon into tiny ice particles. The frozen argon cylinders melted entirely in approximately 40 seconds, when exposed to the mist stream, and liquid argon flowed to the collection area at the bottom of the working tray. Ice particles were collected as a "scum" floating on the surface of the liquid argon. The liquid argon evaporated after 5 minutes.

Example 1 Conclusions

1. A rapid stream of nebulized water droplets (estimated 1 to 1½ m/sec) can be generated by forcing air into a small ultrasonic nebulization chamber using a fan, with a ½ inch exit port placed on the opposite end of the chamber from the fan.
2. The speed and direction of the nebulized water stream can be controlled by changing the internal pressure of the nebulization chamber, and by placing an adjustable pipette in the exit port.

3. Argon frozen into 12 cylinders melted completely in approximately 40 seconds when exposed to a stream of nebulized water particles in air at 74° F. (when lying on a precooled Styrofoam surface).
4. Nebulized water droplets are rapidly frozen into tiny ice particles upon contact with solid argon, when driven as a "mist stream" onto a frozen argon surface at 1 to 1½ m/sec.
5. The tiny ice particles float on the surface of liquid argon in the form of a "scum" of coalescing particles, and can be collected by pooling the melted argon at a lower level than the frozen argon cylinders.

EXAMPLE 2

The heat of sublimation of a solid primary refrigerant (carbon dioxide) was used to rapidly freeze nebulized water droplets. Water droplets were frozen by directing a rapid nebulized stream against the surface of dry ice (frozen carbon dioxide).

Equipment
 1 Styrofoam ice chest (1 gallon)

nebulizer—ultrasonic box fan (5 inch) 120 volt 60 Hz

1 Styrofoam platter 2 lbs dry ice

A similar method as that described in Experiment 1 was used to produce an air driven stream of nebulized water mist (estimated 1 to 1½ m/sec) through the side port glass pipette. The differences were as follows. A dry ice block was placed on the Styrofoam platter. The stream of nebulized mist was directed against the top surface of the dry ice block at a distance of approximately 10 cm for 60 seconds. During this time a moderate amount of condensed "steam" was blown radially away from the nebulized stream contact point on the dry ice surface. Presumably this "steam" was condensed water vapor from around the nebulized droplets in the stream. Frozen ice droplets were not observed bouncing away from the carbon dioxide surface. Nebulized water droplets froze on impact with the surface of the dry ice into tiny ice particles. These particles collected together as a white flaking "scum" along the edges of the shallow crater formed in the dry ice block at the contact point with the nebulized stream.

Example 2 Conclusions

1. When driven as a "mist stream" onto a frozen carbon dioxide surface, nebulized water droplets are rapidly frozen into tiny ice particles.
2. The heat absorbed by carbon dioxide with the solid-to-gas phase change can be used to rapidly freeze small water droplets.
3. The tiny ice particles collect into a white flaking "scum" on the surface of the dry ice around the nebulized stream contact point.

Successful hyper-rapid freezing of nebulized water droplets was achieved using the solid-to-gas phase change heat release of sublimation.

EXAMPLE 3

The solid-to-liquid phase of a cryogenic gas may be used to absorb heat from an oocyte in cell culture media rapidly enough to vitrify the cell. An oocyte is placed in a small biological storage vial containing cell culture media, then plunged directly into a vat of solid/liquid nitrogen slush. Heat is very rapidly absorbed out of the vial (and oocyte) and into the slushed nitrogen without an intervening insulating gas envelope generated around the vial. The heat would be consumed as heat of fusion in the solid to liquid nitrogen phase change, so a nitrogen gas layer would not form around the vial and slow the conduction of heat out of the vial. The high thermoconductivity of the process should be sufficient to increase the freezing rate to allow vitrification of the culture media and the oocyte. Modifications of the system, such as using a copper or silver vial, could be applied to maximize thermoconductivity and freezing rate. Without ice crystal or hyper-concentrated solute damage, the oocyte should survive intact and fertilize normally.

Although the preferred embodiment of the apparatus of the invention has been described above in some detail, it should be appreciated that a variety of embodiments will be readily apparent to one skilled in the art. The description of the apparatus of this invention is not intended to be limiting to this invention, but is merely illustrative of the preferred embodiment.

While the methods for sample preservation and storage have been described in terms of preferred embodiments, it will be apparent to those skilled in the art that variations and modifications may be applied to the methods and in the steps or sequence of steps of the methods described herein without departing from the concept, spirit and scope of the invention.

I claim:

1. A method for freezing a liquid comprising transforming said liquid into very small drops, rapidly driving said very small drops directly onto a refrigerant which is at least partially solidified, and collecting the frozen liquid.

2. The method of claim 1 wherein said at least partially solidified state of said refrigerant is achieved by evaporative cooling in a vacuum chamber.

3. The method of claim 1 wherein said refrigerant is solid.

4. The method of claim 3 wherein said solid refrigerant is undergoing sublimation.

5. The method of claim 1 wherein said transformation into very small drops is accomplished by a nebulizer.

6. The method of claim 1 wherein said transformation into very small drops is accomplished by a flow cytometer.

7. The method of claim 1 wherein said refrigerant is a slush comprising a mixture of solid and liquid.

8. The method of claim 7 wherein said solid and liquid are the same element or compound.

9. The method of claim 7 wherein said solid and liquid are different elements or compounds.

10. A method for preserving a sample suspension of biological material comprising transforming said sample suspension into very small drops, rapidly driving said very small drops directly onto a refrigerant which is at least partially solidified, and collecting the frozen sample.

11. The method of claim 10 wherein transforming the sample suspension into very small drops is accomplished by a nebulizer.

12. The method of claim 10 wherein transforming the sample suspension into very small drops is accomplished by a flow cytometer.

13. The method of claim 10 wherein said refrigerant is a solid.

14. The method of claim 10 wherein said refrigerant is a slush comprising a mixture of solid and liquid.

15. The method of claim 14 wherein said solid and liquid are the same element or compound.

16. The method of claim 14 wherein said solid and liquid are different elements or compounds.

17. The method of claim 10 wherein the refrigerant is inert and nonreactive.

18. The method of claim 17, wherein the inert and nonreactive refrigerant is a noble gas.

19. The method of claim 18, wherein the noble gas is argon.

20. The method of claim 17, wherein said inert and nonreactive refrigerant is nitrogen.

21. The method of claim 20 wherein said nitrogen is a slush and is achieved by placing liquid nitrogen under a partial vacuum.

22. The method of claim 10 wherein the refrigerant is solid carbon dioxide.

23. The method of claim 10 wherein the refrigerant comprises a primary and secondary refrigerant, wherein the secondary refrigerant is held at a temperature below the freezing point of the primary refrigerant, said secondary refrigerant achieving the solid or slushed state of the primary refrigerant through thermal contact with the primary refrigerant.

24. The method of claim 23 wherein said primary refrigerant is argon and said secondary refrigerant is nitrogen.

25. The method of claim 10 wherein a cryopreservative is added to the sample prior to the step of driving the sample onto refrigerant.

26. The method of clam 10 wherein said refrigerant is oxygen or hydrogen.

27. The method of claim 10 wherein said refrigerant is organic.

28. The method of claim 27 wherein said organic refrigerant is selected from the group consisting of liquid carbon dioxide, propane, butene, ethane, Freon, and ethanol.

29. The method of claim 10 wherein said refrigerant is mercury or lead.

30. The method of claim 10 wherein said refrigerant is selected from the group consisting of helium, neon, nitrogen, argon, krypton, and xenon.

31. A method of stopping a liquid chemical or biological reaction comprising rapidly cooling the reaction mixture such that the chemical or biological activity stops; wherein said cooling is achieved by transforming the reaction mixture into very small drops, driving the very small drops directly onto a refrigerant which is at least partially solidified, and collecting the cooled reaction mixture.

32. The method of claim 31 wherein a nebulizer is used to achieve the very small drops of liquid reaction mixture.

33. The method of claim 31 wherein a flow cytometer is used to achieve the very small drops of liquid reaction mixture.

34. A method for lyophilizing a suspension of compounds or compositions while retaining structural integrity comprising:
(a) rapidly driving the suspension directly onto a refrigerant to freeze the suspension, wherein said refrigerant is at least partially solidified;
(b) collecting the frozen suspension; and
(c) drying the frozen suspension.

35. The method of claim 34 further comprising the step of transforming the suspension into very small drops prior to the step of driving the suspension onto the refrigerant.

36. An apparatus for freezing a sample suspension, including biological samples, comprising a means for rapidly driving the sample suspension through an outlet, and a container for refrigerant positioned such that the outlet delivers the sample directly onto the refrigerant and the refrigerant is at least partially solidified.

37. The apparatus of claim 36 further comprising a means for transforming the sample suspension into very small drops.

38. The apparatus of claim 36 wherein said refrigerant is solid.

39. The apparatus of claim 36 wherein said refrigerant is a slush comprising a mixture of solid and liquid.

40. An apparatus for freezing a suspension of biological material comprising a flow cytometer positioned over a container holding refrigerant, wherein when activated, the flow cytometer transports the suspension of biological material directly onto the refrigerant.

41. The apparatus of claim 40 wherein said refrigerant is solid.

42. The apparatus of claim 40 wherein said refrigerant is a slush comprising a mixture of solid and liquid.

43. The apparatus of claim 40 further comprising a container containing the suspension of biological material, said container communicatively coupled to the flow cytometer.

44. An apparatus for freezing a suspension of biological material comprising a nebulizer and a container holding refrigerant, wherein when activated, the nebulizer transports the suspension of biological material directly onto the refrigerant, wherein said refrigerant is at least partially solidified.

45. The apparatus of claim 44 further comprising a container containing the suspension of biological material, said container communicatively coupled to the nebulizer.

46. The apparatus of claim 44 wherein said container holding refrigerant comprises a container holding a primary and a secondary refrigerant, wherein the secondary refrigerant is held at a temperature below the freezing point of the primary refrigerant, said secondary refrigerant achieving at least a partially solidified state of the primary refrigerant through thermal contact; wherein the nebulizer transports the suspension of biological material directly onto the primary refrigerant.

47. The apparatus of claim 46 comprising separate containers for the primary and secondary refrigerant, wherein said container of secondary refrigerant is in thermal contact with the primary refrigerant, said secondary refrigerant causing said primary refrigerant to achieve at least a partially solidified state.

48. An apparatus for preserving a sample suspension comprising:
(a) a sample chamber communicatively coupled to a nebulizer;
(b) a container holding refrigerant which is at least partially solidified; and
(c) a sample outlet;
wherein said nebulizer, when activated, transports the liquid sample from the sample chamber through the sample outlet directly onto the refrigerant.

49. The apparatus of claim 48 wherein the sample chamber has openings for regulating the speed of the sample exiting the sample chamber through the sample outlet.

50. The apparatus of claim 48 wherein the sample chamber is associated with a fan for regulating the speed of the sample exiting the sample chamber through the sample outlet.

51. The apparatus of claim 48 wherein said at least partially solidified refrigerant is achieved through a primary refrigerant in a container which is in thermal contact with a secondary refrigerant held at a temperature below the freezing point of the primary refrigerant, causing the primary refrigerant to achieve at least a partially solidified state, wherein the nebulized sample directly contacts the primary refrigerant.

52. An apparatus for freezing a sample suspension, including biological samples, comprising a means for transforming the sample suspension into very small drops, means for creating a saturated or humidified gas medium flowing onto refrigerant which is at least partially solidified, means for rapidly driving the very small drops of sample suspension; within the gas medium, through an outlet, and a container for the refrigerant, wherein the sample outlet delivers the sample directly onto the refrigerant.

53. An apparatus for freezing a sample suspension, including biological samples, comprising a means for transforming the sample suspension into very small drops, means for rapidly driving the very small drops of sample suspension, through an outlet, and a container for the refrigerant, wherein the sample outlet delivers the sample directly onto the refrigerant, wherein said means for rapidly driving the very small drops of sample suspension through an outlet comprises a nebulizer attached to a sample delivery means, and wherein said container for refrigerant comprises a hollow sphere for holding primary refrigerant, with an opening for inserting said nebulizer, said sphere positioned within a container for secondary refrigerant such that the sphere is at least partially submerged in the secondary refrigerant.

54. An apparatus for freezing a liquid sample, including biological samples, comprising:

(a) a rotating drum filled with liquid secondary refrigerant, said drum positioned inside a housing half-filled with liquid primary refrigerant such that said drum is partially submerged in the primary refrigerant; and (b) one or more nebulizers positioned over the exposed surface of the drum; wherein in use, as the drum rotates, the secondary refrigerant inside causes a layer of frozen primary refrigerant to form on the exposed surface, and sample is sprayed from said nebulizers onto frozen primary refrigerant on the surface of the drum, as the drum rotates, the frozen sample floats off into the liquid primary refrigerant.

55. An apparatus for freezing a liquid sample, including biological samples, comprising:

(a) a housing with a sloped upper surface comprising grooves, the end walls of the grooves having openings connected to a pipe at the upper end, and to a trough at the lower end, said housing being hollow with inlet and outlet ports for circulating liquid secondary refrigerant through the housing; and (b) multiple nebulizers, one positioned over each groove; wherein liquid primary refrigerant is transported from the pipe through the openings, down the grooves where it freezes due to the liquid secondary refrigerant circulating through the housing, and sample is sprayed onto the frozen primary refrigerant in the grooves, causing the refrigerant to melt and flow into the trough.

56. An apparatus for freezing a liquid sample, including biological samples, comprising:

(a) a housing, said housing divided into first and second sections, the first section filled with liquid secondary refrigerant, and the second section partially filled with liquid primary refrigerant;

(b) a rotating metal disk positioned half in the first section and half in the second section such that the disk is in contact with both the primary and secondary refrigerants, said secondary refrigerant cooling the metal disk causing a layer of frozen primary refrigerant to form on the exposed surface of the disk; and (c) one or more nebulizers positioned in the second housing section containing primary refrigerant such that sample is sprayed from the nebulizers onto the frozen primary refrigerant coating the exposed portion of the disk.

57. An apparatus for freezing a liquid sample, including biological samples, comprising:

(a) a vertical cylindrical pipe within a larger cylindrical container, said container comprising a lower section filled with liquid secondary refrigerant and an upper section, said pipe positioned such that a top opening of the pipe is in the upper section of the cylindrical container and a bottom opening of the pipe is below the lower section of the cylindrical container;

(b) insulation surrounding the cylindrical container;

(c) a conduit connected to the lower section of the cylindrical container, said conduit transporting the liquid secondary refrigerant; and (d) a nebulizer positioned over the top opening in the pipe; wherein liquid primary refrigerant is forced under pressure up into the pipe where it freezes as it passes through the lower section of the cylindrical container filled with secondary refrigerant, and said frozen primary refrigerant is extruded out of the top opening of the pipe, said sample is sprayed onto the extruded primary refrigerant.

58. An apparatus for freezing a liquid sample, including biological samples, comprising a centrifuge with paddles holding solid primary refrigerant connected to the rotor, and one or more nebulizers positioned in the walls of the centrifuge such that sample delivered to the nebulizers is sprayed onto the solid refrigerant as the rotor turns.

59. An apparatus for freezing a liquid sample, including biological samples, comprising a column attached to a rotating head comprising multiple horizontal nebulizers positioned over a cylindrical container, the walls of which are coated with solid refrigerant; sample is delivered to the nebulizers through the column and sprayed onto the solid refrigerant coating the walls of the container as the head rotates.

60. An apparatus for freezing a liquid sample, including biological samples, comprising:

(a) a housing filled with liquid secondary refrigerant;

(b) one or more hollow rotating cylinders positioned such that they are submerged in the liquid secondary refrigerant;

(c) inlet tubes for sample transfer connected to respective cylinders;

(d) nebulizers positioned on said inlet tubes inside the cylinders to deliver sample to the inside walls of the cylinders; wherein liquid primary refrigerant is placed inside the cylinders, and as the cylinders rotate, the primary refrigerant freezes on the walls; sample sprayed onto the cylinder wall freezes and drops into the remaining liquid refrigerant at the bottom of the rotating cylinder.

61. An apparatus for freezing a liquid sample, including biological samples, comprising a rotating cylindrical receptacle with solid refrigerant coating the inner walls, and a sample delivery tube with an injection aperture at the end; wherein said delivery tube is positioned such that the injection aperture is in close proximity to the solid refrigerant coating the receptacle walls.

62. An apparatus for freezing a liquid sample, including biological samples, comprising:

(a) a receptacle holding slushed refrigerant;

(b) a cylinder with small injection apertures located at one end, positioned in the receptacle such that the injection apertures are submerged in the slushed refrigerant; wherein pressurized sample is delivered through the injection apertures in the cylinder into the slushed refrigerant.

63. An apparatus for freezing a liquid sample, including biological samples, comprising:

(a) a receptacle holding slushed refrigerant, said receptacle having small injection apertures in the bottom; and (b) an injection apparatus connected to the bottom of said receptacle, said injection apparatus comprising nebulizer jets; wherein sample is injected into the slushed refrigerant in the receptacle by means of said nebulizer jets.

64. An apparatus for freezing a liquid sample, including biological samples, comprising a container for refrigerant positioned inside a vacuum chamber, said vacuum chamber having a nebulizer connected thereto, wherein the nebulizer is positioned over the container for refrigerant.

* * * * *